US007066945B2

(12) United States Patent
Hashiba et al.

(10) Patent No.: US 7,066,945 B2
(45) Date of Patent: Jun. 27, 2006

(54) INTRAGASTRIC DEVICE FOR TREATING OBESITY

(75) Inventors: Kiyoshi Hashiba, Sao Paulo (BR); Vihar C. Surti, Winston-Salem, NC (US)

(73) Assignee: Wilson-Cook Medical Inc., Winston-Salem, NC (US)

( * ) Notice: Subject to any disclaimer, the term of this patent is extended or adjusted under 35 U.S.C. 154(b) by 151 days.

(21) Appl. No.: 10/151,720

(22) Filed: May 17, 2002

(65) Prior Publication Data

US 2003/0078611 A1    Apr. 24, 2003

Related U.S. Application Data

(60) Provisional application No. 60/291,790, filed on May 17, 2001, provisional application No. 60/360,353, filed on Feb. 27, 2002.

(51) Int. Cl.
*A61M 29/00* (2006.01)

(52) U.S. Cl. .................................... 606/191

(58) Field of Classification Search ............ 606/191, 606/192, 195, 157, 184, 185, 194; 128/898
See application file for complete search history.

(56) References Cited

U.S. PATENT DOCUMENTS

| | | | |
|---|---|---|---|
| 2,508,690 A | 5/1950 | Schmerl | |
| 4,133,315 A | 1/1979 | Berman et al. | |
| 4,246,893 A | 1/1981 | Berson | |
| 4,315,509 A | 2/1982 | Smit | |
| 4,403,604 A | 9/1983 | Wilkinson et al. | |
| 4,416,267 A | 11/1983 | Garren et al. | |
| 4,485,805 A | 12/1984 | Foster, Jr. | |
| 4,558,699 A | 12/1985 | Bashour | |
| 4,607,618 A | 8/1986 | Angelchik | |
| 4,694,827 A | 9/1987 | Weiner et al. | |
| 4,696,288 A | 9/1987 | Kuzmak et al. | |

(Continued)

FOREIGN PATENT DOCUMENTS

WO    WO 87/00034    1/1987

OTHER PUBLICATIONS

"Intragastric balloons for morbid obesity: results, patient tolerance and balloon life span," E.M.H. Mathus-Vliegen and G.N.J. Tytgat, Br. J. Surg., vol. 77, No. 1, pp. 76-79, Jan. 1990.

(Continued)

*Primary Examiner*—Anhtuan T. Nguyen
*Assistant Examiner*—Charles Sam
(74) *Attorney, Agent, or Firm*—Brinks Hofer Gilson & Lione

(57) ABSTRACT

An apparatus and method comprising at least one intragastric member or artificial bezoar made of a digestive-resistant or substantially indigestible material that is introduced into a gastric lumen of a mammal for the treatment of obesity. The intragastric member or artificial bezoar is typically at inserted into the gastric lumen in a partially compacted configuration, whereby it is then manipulated into, or allowed to assume, a second expanded configuration sufficiently large to remain within the reservoir of the stomach during normal activities and not be passed through the pylorus into the intestines. In animals, the present invention has been found to be effective in achieving weight loss over a several month period, while being easy to place and retrieve.

19 Claims, 13 Drawing Sheets

U.S. PATENT DOCUMENTS

| | | |
|---|---|---|
| 4,723,547 A | 2/1988 | Kullas et al. |
| 4,803,985 A | 2/1989 | Hill |
| 4,878,905 A | 11/1989 | Blass |
| 4,899,747 A | 2/1990 | Garren et al. |
| 4,925,446 A | 5/1990 | Garay et al. |
| 5,129,915 A | 7/1992 | Cantenys |
| 5,234,454 A | 8/1993 | Bangs |
| 5,246,456 A | 9/1993 | Wilkinson |
| 5,306,300 A | 4/1994 | Berry |
| 5,868,141 A * | 2/1999 | Ellias .................. 128/898 |
| 6,427,089 B1 | 7/2002 | Knowlton |
| 6,450,946 B1 | 9/2002 | Forsell |
| 6,454,699 B1 | 9/2002 | Forsell |
| 6,540,789 B1 | 4/2003 | Silverman et al. |
| 6,558,400 B1 | 5/2003 | Deem et al. |
| 6,627,206 B1 | 9/2003 | Lloyd |
| 6,656,194 B1 | 12/2003 | Gannoe et al. |
| 6,675,809 B1 | 1/2004 | Stack et al. |
| 6,676,674 B1 | 1/2004 | Dudai |
| 6,733,512 B1 | 5/2004 | McGhan |
| 6,740,121 B1 | 5/2004 | Geitz |
| 6,746,460 B1 | 6/2004 | Gannoe et al. |
| 6,755,869 B1 | 6/2004 | Geitz |
| 6,802,868 B1 | 10/2004 | Silverman et al. |
| 2001/0011543 A1 | 8/2001 | Forsell |
| 2002/0055757 A1 | 5/2002 | de la Torre et al. |
| 2002/0183768 A1 | 12/2002 | Deem et al. |
| 2002/0188354 A1 | 12/2002 | Peghini |
| 2003/0021822 A1 | 1/2003 | Lloyd |
| 2003/0040808 A1 | 2/2003 | Stack et al. |
| 2003/0049325 A1 | 3/2003 | Wolfgang et al. |
| 2003/0109892 A1 | 6/2003 | Deem et al. |
| 2003/0109935 A1 | 6/2003 | Geitz |
| 2003/0120265 A1 | 6/2003 | Deem et al. |
| 2003/0158569 A1 | 8/2003 | Wazne |
| 2003/0158601 A1 | 8/2003 | Silverman et al. |
| 2003/0171768 A1 | 9/2003 | McGhan |
| 2003/0199989 A1 | 10/2003 | Stack et al. |
| 2003/0199990 A1 | 10/2003 | Stack et al. |
| 2003/0199991 A1 | 10/2003 | Stack et al. |
| 2004/0019388 A1 | 1/2004 | Starkebaum |
| 2004/0024386 A1 | 2/2004 | Deem et al. |
| 2004/0030347 A1 | 2/2004 | Gannoe et al. |
| 2004/0039452 A1 | 2/2004 | Bessler |
| 2004/0044353 A1 | 3/2004 | Gannoe |
| 2004/0044354 A1 | 3/2004 | Gannoe et al. |
| 2004/0044357 A1 | 3/2004 | Gannoe et al. |
| 2004/0059289 A1 | 3/2004 | Garza |
| 2004/0082963 A1 | 4/2004 | Gannoe et al. |
| 2004/0092892 A1 | 5/2004 | Kagan et al. |
| 2004/0092974 A1 | 5/2004 | Gannoe et al. |
| 2004/0093091 A1 | 5/2004 | Gannoe et al. |
| 2004/0117031 A1 | 6/2004 | Stack et al. |
| 2004/0122452 A1 | 6/2004 | Deem et al. |
| 2004/0122453 A1 | 6/2004 | Deem et al. |
| 2004/0122526 A1 | 6/2004 | Imran |
| 2004/0138760 A1 | 7/2004 | Schurr |
| 2004/0138761 A1 | 7/2004 | Stack et al. |
| 2004/0143342 A1 | 7/2004 | Stack et al. |
| 2004/0148034 A1 | 7/2004 | Kagan et al. |
| 2004/0153106 A1 | 8/2004 | Dudai et al. |
| 2004/0153167 A1 | 8/2004 | Stack et al. |
| 2004/0158331 A1 | 8/2004 | Stack et al. |
| 2004/0172141 A1 | 9/2004 | Stack et al. |
| 2004/0172142 A1 | 9/2004 | Stack et al. |
| 2004/0172143 A1 | 9/2004 | Geitz |
| 2004/0186502 A1 | 9/2004 | Sampson et al. |
| 2004/0186503 A1 | 9/2004 | DeLegge |
| 2004/0204768 A1 | 10/2004 | Geitz |
| 2004/0210243 A1 | 10/2004 | Gannoe et al. |
| 2004/0220682 A1 | 11/2004 | Levine et al. |

OTHER PUBLICATIONS

"Clinical trial of silicone-rubber gastric balloon to treat obesity," Allan Geliebter, Pamela M. Melton, Richard S. McCray, Dennis Gage, Steven B. Heymsfield, Michael Abiri and Sami A. Hashim, International Journal of Obesity, 15, pp. 259-266, 15, pp. 259-266 (1991).

"Endoscopic Management of Huge Bezoars," Y.G. Want, U. Seitz, Z. L. Li, N. Soehendra, X.A. Qiao, Endoscopy 1988: 30: pp. 371-374.

"Gastric distension, hunger and energy intake after balloon implantation in severe obesity," D. Rigaud, N. Trostler, R. Rozen, T. Vallott and M. Apfelbaum.

"Intragastric Devices for Weight Loss: Fact of Fancy?", The American Journal of Gastroenterology, vol. 83, No. 5, pp. 554-555, 1988.

"Distal Gastric Bypass/Duodenal Switch," Robert A. Rabkin, MD, FACS, Surgery For Morbid Obesity, 2 pages, 2001.

"Bioenterics Intragastric Balloon," 2 pages, 2000.

"Fat drugs: New treatments for obesity are making their way to your doctor. Can they work for you?", Monica Matys, 2 pages, 2000.

"Bezoar," drkoop.com, 1 page.

"Obesity: The World's Oldest Metabolic Disorder," Michael Blumenkrantz, M.D., F.A.C.P., F.A.C.N., 5 pages.

"Surgical treatments for obesity," 3 pages, WebMD, 1999.

"Experimental Study An Alternative Endocscopic Method for The Treatement Of Obesity: The Butterfly Technique,".

* cited by examiner

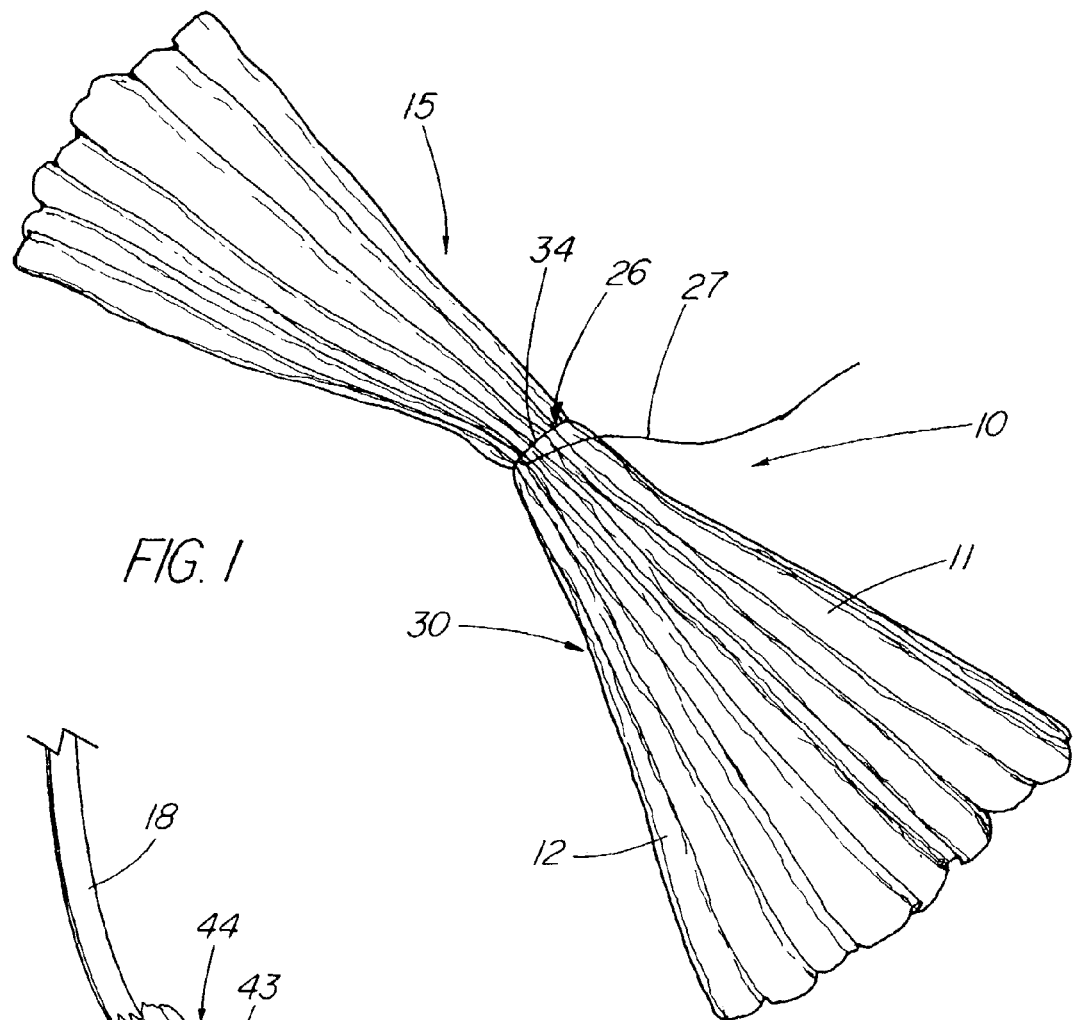
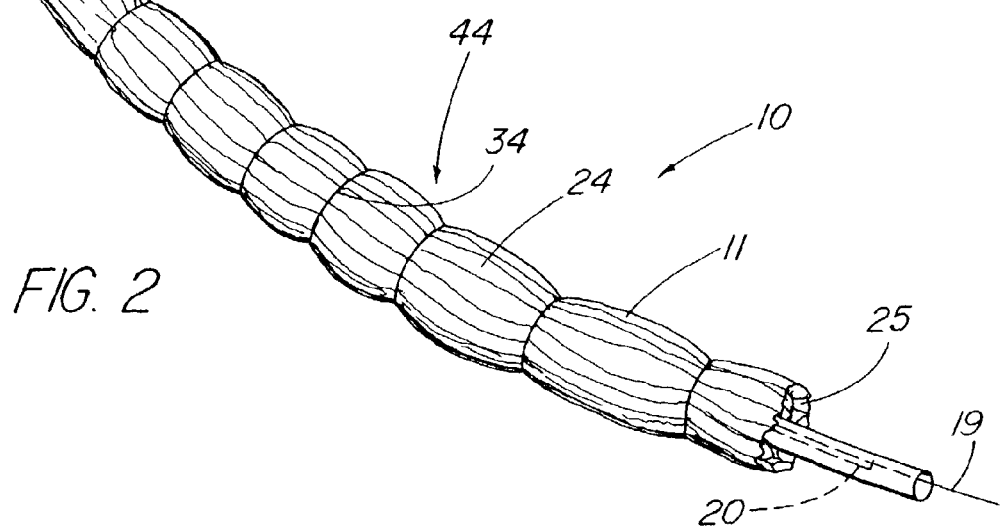

INTRAGASTRIC DEVICE FOR TREATING OBESITY

RELATED APPLICATIONS

This application claims the benefit of U.S. Provisional Application No. 60/291,790 filed May 17, 2001, and U.S. Provisional Application No. 60/360,353 filed Feb. 27, 2002, both entitled "Intragastric Device For Treating Obesity".

TECHNICAL FIELD

This invention relates to medical devices, and more particularly to obesity treatment devices that can be placed in the stomach of a patient to reduce the size of the stomach reservoir.

BACKGROUND OF THE INVENTION

It is well known that obesity is a very difficult condition to treat. Methods of treatment are varied, and include drugs, behavior therapy, and physical exercise, or often a combinational approach involving two or more of these methods. Unfortunately, results are seldom long term, with many patients eventually returning to their original weight over time. For that reason, obesity, particularly morbid obesity, is often considered an incurable condition. More invasive approaches have been available which have yielded good results in many patients. These include surgical options such as bypass operations or gastroplasty. However, these procedures carry high risks, and are therefore not appropriate for most patients.

In the early 1980s, physicians began to experiment with the placement of intragastric balloons to reduce the size of the stomach reservoir, and consequently its capacity for food. Once deployed in the stomach, the balloon helps to trigger a sensation of fullness and a decreased feeling of hunger. These balloons are typically cylindrical or pear-shaped, generally range in size from 200–500 ml or more, are made of an elastomer such as silicone, polyurethane, or latex, and are filled with air, water, or saline. While some studies demonstrated modest weight loss, the effects of these balloons often diminished after three or four weeks, possibly due to the gradual distension of the stomach or the fact that the body adjusted to the presence of the balloon. Other balloons include a tube exiting the nasal passage that allows the balloon to be periodically deflated and re-insufflated to better simulate normal food intake. However, the disadvantages of having a inflation tube exiting the nose are obvious.

The experience with balloons as a method of treating obesity has provided uncertain results, and has been frequently disappointing. Some trials failed to show significant weight loss over a placebo, or were ineffective unless the balloon placement procedure was combined with a low-calorie diet. Complications have also been observed, such as gastric ulcers, especially with use of fluid-filled balloons, and small bowel obstructions caused by deflated balloons. In addition, there have been documented instances of the balloon blocking off or lodging in the opening to the duodenum, wherein the balloon may act like a ball valve to prevent the stomach contents from emptying into the intestines.

Unrelated to the above-discussed methods for treating obesity, it has been observed that the ingestion of certain indigestible matter, such as fibers, hair, fuzzy materials, etc., can collect in the stomach over time, and eventually form a mass called a bezoar. In some patients, particularly children and the mentally handicapped, bezoars often result from the ingestion of plastic or synthetic materials. In many cases, bezoars can cause indigestion, stomach upset, or vomiting, especially if allowed to grow sufficiently large. It has also been documented that certain individuals having bezoars are subject to weight loss, presumably due to the decrease in the size of the stomach reservoir. Although bezoars may be removed endoscopically, especially in conjunction with a device known as a bezotome or bezotriptor, they, particularly larger ones, often require surgery.

What is needed is a intragastric member that provides the potential weight loss benefits of a bezoar or intragastric balloon without the associated complications. Ideally, such a-device should be well-tolerated by the patient, effective over a long period of time, sizable for individual anatomies, and easy to place and retrieve.

SUMMARY OF THE INVENTION

The foregoing problems are solved and a technical advance is achieved by an illustrative obesity treatment apparatus comprising at least one intragastric member or artificial bezoar made of a digestive-resistant or substantially indigestible material that is introduced into a gastric lumen of a mammal in a first configuration. The intragastric member or artificial bezoar is typically inserted into the gastric lumen in a partially compacted configuration, whereby it is then manipulated into, or allowed to assume, a second expanded configuration sufficiently large to remain within the reservoir of the stomach during normal activities and not be passed through the pylorus and into the intestines. In animals, the present invention has been found to be effective in achieving weight loss over a several month period, while being easy to place and retrieve. Another advance is that the present invention can be effective at a smaller volume within the stomach than existing intragastric members, such as balloons.

In one aspect of the invention, the obesity treatment apparatus comprises a plurality of elongate plastic strips joined in the middle by a retaining mechanism, such as a nylon thread, so that the intragastric device has a shape suggestive of a butterfly or bow-tie. Alternatively, the intragastric member can comprise a folded or pleated sheet, elongated fibers or hairs, or other materials that can assume the expanded configuration while not causing trauma to the stomach wall of the patient.

In another aspect of the invention, the obesity treatment apparatus comprises a plurality of intragastric members, such as the embodiments described above, which are coupled together in a set or grouping within the gastric lumen. The intragastric members are introduced individually into the gastric lumen, and then attached using a coupling mechanism, which may extend from the intragastric members themselves, or they can be introduced as a set, depending on the diameter and design used. A tether tied to the device, such a nylon thread (e.g., fishing line), can be used to assist in coupling the plurality of intragastric members together. Additional components may also be used with the coupling mechanism to facilitate placement of the set and/or separation of the individual intragastric members. For example, specially configured plastic or metal pieces can be attached to the line bundling the set of intragastric members together to enhance visibility of the line for cutting with a endoscopic scissor or scalpel, or to provide a hard surface against which the cutting instrument can be applied to more easily sever the line. Irrespective of whether the obesity treatment device includes a single intragastric member, or a coupling of intragastric members, the principal requirement is that, once in the stomach, it attains a shape and size that cannot pass through or lodge in the pyloric sphincter.

In another aspect of the invention, the obesity treatment device includes a delivery system, such as one or more catheters, to place the intragastric members within the gastric lumen. In one embodiment, one or more intragastric members are mounted on a catheter or overtube and secured with cotton threads extending through the passageway of the delivery catheter via oppositely placed apertures. A metal wire or loop is then withdrawn, severing the threads and releasing the intragastric member(s) into the gastric lumen. The individual intragastric members are then coupled together by drawing them together via the attached tethering threads, then secured with a device such as a rubber patch pushed by an introduced metal tube or similar device.

Other delivery systems of the present invention involve constraining the intragastric members, then releasing them in the gastric lumen. These can include pushing the intragastric member(s) from an outer delivery catheter, typically by use of pusher member within the delivery catheter passageway. Other methods include constraining the intragastric member(s) with a splittable or dissolvable film or sheath that allows that device to be deployed in a compact configuration, then allowed to expand when the outer wrapping or sheath is split by the operator, or is allowed to dissolve away over time in the stomach. In the latter example, a delivery catheter may not be necessary.

While a delivery catheter or other delivery system can be used to deliver the intragastric members of the present invention, it has been shown that the intragastric members can generally be placed endoscopically or blindly by pulling them into the gastric lumen using a pair of forceps or some other retrieval grasping or device.

In yet another aspect of the invention, the intragastric member can comprise a plurality of expandable members that are constrained into a first configuration for introduction into the gastric lumen, whereby the device is manipulated to allow it to assume a second, expanded configuration for residing in the stomach. One such example is an intragastric member having a plurality of strips arranged concentrically and secured at each end with a tether fixedly attached at the first end and extending through an internal portion of the device. The second end attachment is adapted to slide over the tether, and can be drawn or urged toward the first end attachment to cause the expandable members to bow outward so as to increase the overall volume of the device.

In still yet another aspect of the invention, the intragastric members can be pre-coupled together with a coupling mechanism, such as a nylon fishing line, prior to introduction into the gastric lumen. Because the volume of the grouping in the stomach increases over time due to mucous accumulation or other factors, a single device having the overall size of the grouping (e.g., four devices grouped together) may not be readily removed. However, by severing the line comprising the grouping mechanism, the individual intragastric devices of the grouping can be removed one at a time by using an endoscope and retrieval device.

In yet another aspect of the invention, the intragastric member can comprise a single strip of material having a series of apertures space along the length thereof, wherein the strip of material is bundled into a series of folds by passing a nylon thread through the apertures and cinching the strip of material together. The intragastric member is inserted into the gastric lumen by passing the apertures of the strip of material over a wire guide, preferably in separate bundles, until the entire strip has been accumulated and bundled together inside the gastric lumen with a nylon thread. The nylon thread can be cut to allow the bundles to separate, thereby facilitating its removal by grasping and pulling one end of the strip.

It has also been contemplated that more than one grouping may be used at a time. For example, two or more independent groupings of intragastric devices floating freely in the stomach may be utilized.

These and other advantages, as well as the invention itself, will become apparent in the details of construction and operation as more fully described below. Moreover, it should be appreciated that several aspects of the invention can be used with other types of intragastric devices or procedures used for the treatment of obesity.

BRIEF DESCRIPTION OF SEVERAL VIEWS OF THE DRAWINGS

Several embodiments of the present invention will now be described by way of example with reference to the accompanying drawings, in which:

FIG. 1 depicts a pictorial view of an intragastric member of the present invention;

FIG. 2 depicts a pictorial view of the embodiment of FIG. 1 with a delivery system;

DETAILED DESCRIPTION OF THE INVENTION

Figure 3:
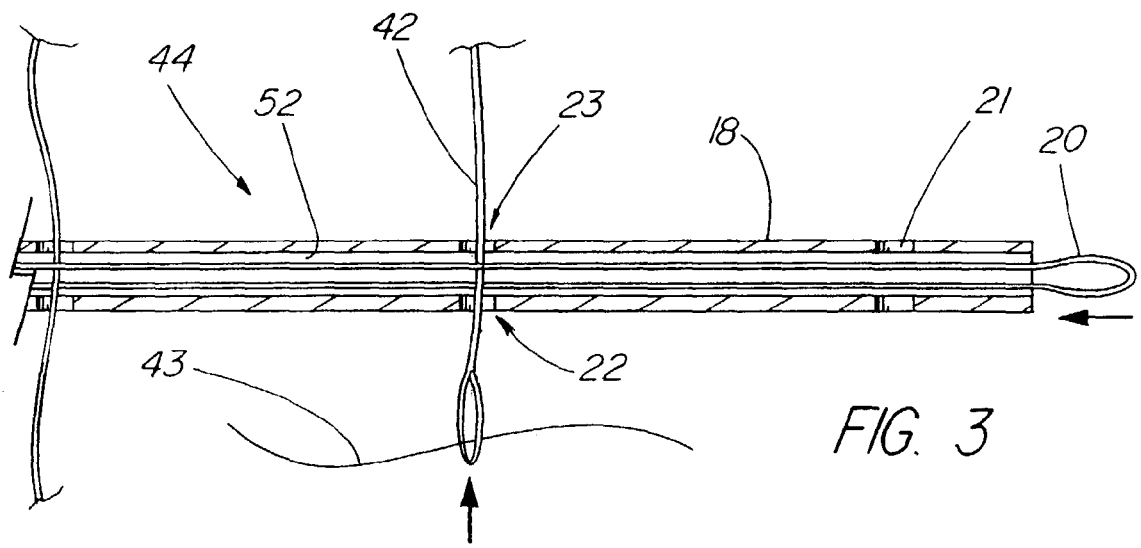
FIG. 3 depicts a sectional view of the delivery system of FIG. 2.

The obesity treatment apparatus 10 of the present invention depicted in FIGS. 1–25 comprises one or more intragastric members 11, each comprising one or more digestive-resistant or indigestible member 12 sized and configured such that the intragastric member 11 can be placed into the stomach of a mammalian patient and reside therein, and being generally unable to pass through the pylorus. As used herein, the terms digestive-resistant and indigestible are intended to mean that the material used is not subject to the degrative effects of stomach acid and enzymes, or the general environment found within the gastric system over an extended period of time, therefore allowing the device to remain intact for the intended life of the device. This does not necessarily mean that the material cannot be degraded over time; however, one skilled in medical arts and gastrological devices would readily appreciate the range of material that would be suitable for use as a long-term intragastric member.

Many well-known plastics have suitable properties, including selected polyesters, polyurethanes, polyethylenes, polyamides, silicone, or other possible materials. Mammalian hair has been found to form natural bezoars, and thus, is also a possible material. However, some materials, such as certain polyamides, have been found to expand over time, which can be an undesirable property. Most other natural materials are generally much less resistant to acids and enzymes, and would therefore typically require treatment or combination with resistant materials to function long term, unless a shorter-term placement is intended or desired.

In the preferred embodiments, the digestive-resistant or indigestible member 12 comprises a low density polyethylene having a thickness of about 40–50 microns. Fluorinated ethylene propylene, ethylene vinyl acetate copolymer, nylon, or types of polymers that are biocompatible and to which food will generally not adhere may also be utilized.

FIG. 1 depicts a single intragastric member 11 in which the digestive-resistant members 12 include a plurality of elongate plastic strips 30 that are secured together in the middle by a retaining element 34, such as a nylon thread. The thread can be elongated to serve as a coupling mechanism 26, such as a tether 27. The number of digestive-resistant members 12 or strips 30 used to form the intragastric member 11 depends on the material used, their length and width, and how many intragastric members 11 comprise a set or grouping. The optimal length of the intragastric member 11 is determined by considering these same factors, as well by what is determined through experimentation to work best.

Feasibility studies have been primarily limited to placement in pigs with both 8 cm and 16 cm intragastric members being used, both having a total volume of about 40 ml when placed in the stomach of the animal. Although the experiments were designed to establish the safety of the device, significant weight loss was nevertheless observed in the test animals. Although no gastric ulcers were found in animals with polyester intragastric members, there was a 20% incidence of gastric ulcers in animals having polyamide devices.

Figure 6:
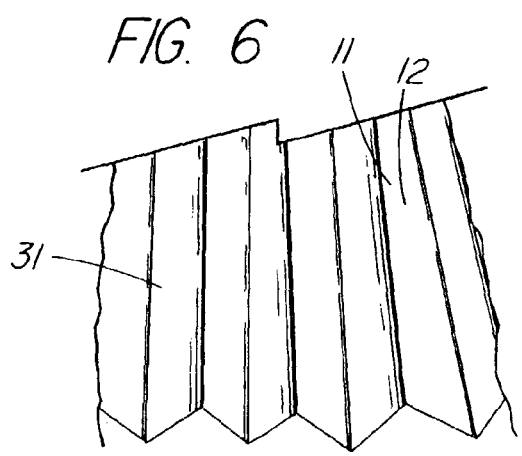
FIGS. 6–7 depict detail views of different embodiments of indigestible members of intragastric members of the present invention.
Figure 7:
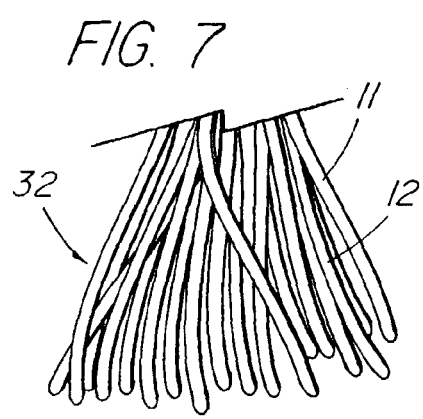

Results from human trials may lead to modifications in the configuration being depicted in the figures of this application. Nevertheless, it is already understood that the dimensions shape, and construction of the intragastric member can be quite variable and still produce the desired results. For example, FIGS. 6–7 depict an alternative digestive-resistant member 12. In the embodiment shown in FIG. 6, the strips 30 of FIG. 1 are replaced by digestive-resistant member 12 comprising a folded or pleated sheet 31 of plastic or other material. Either a single sheet 31 or multiple sheets can be used to form the intragastric member 11 of this embodiment. The embodiment shown in FIG. 7 depicts an intragastric member 11 in which the digestive-resistant members 12 comprise a plurality of elongated fibers or hairs 32, typically made of polymer or other synthetic material.

Figure 8:
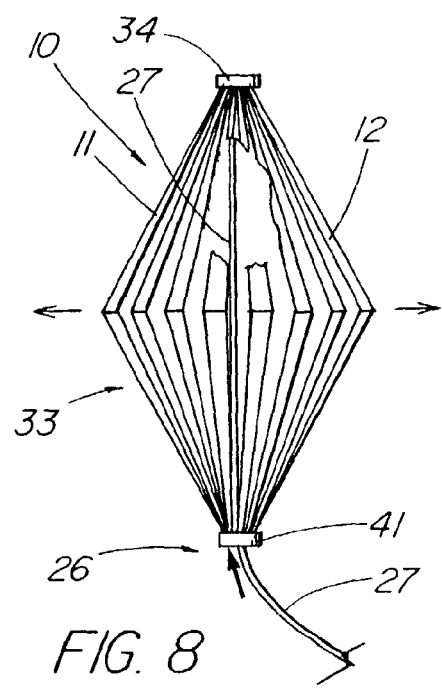
FIG. 8 depicts a partially sectioned side view of an expandable intragastric member of the present invention.

In the illustrative embodiments, the retaining element 34 (see FIG. 1) is located about the center of the device to hold the digestive-resistant members 12 together. However, a skilled artisan would appreciate that other designs utilizing differently placed retaining elements 34, or eliminating them entirely, could also be utilized. For example, FIG. 8 depicts an expandable device 33 that comprises a retaining element 34 at one end to secure the digestive-resistant members 12, which in this embodiment are typically made of a material having a certain degree of stiffness. The other end is secured by a second, slidable retaining element 41 that is disposed over a tether 27 attached to the first retaining member 34. The intragastric member 11 is deployed in an elongated configuration with the retaining elements 34, 41 located near their maximum possible difference apart. After the device is placed in the gastric lumen, the slidable retaining element 41 is urged along the tether 27 and toward the first retaining element 34 by using a tube, probe, or other device, until the digestive-resistant members 12 have bowed outward, thus increasing the overall dimensions and volume of the device. The slidable retaining element 41 continues to grip the tether 27 after the urging mechanism is removed, retaining the increased dimensions of the intragastric member 11 until further manipulation is needed to reduce its diameter for removal from the patient.

Figure 4:
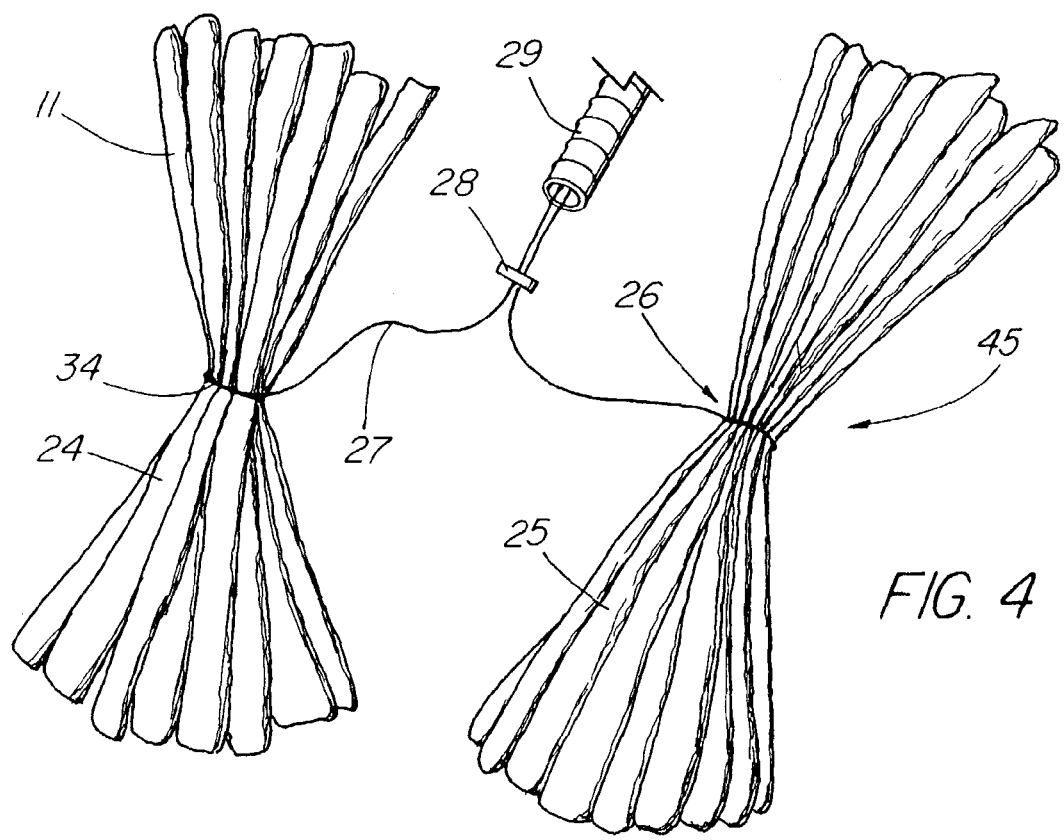
FIGS. 4–5 depicts a pictorial view of a pair of intragastric members of the present invention prior to, and after being coupled together.

Deployment of intragastric member 11 can be accomplished in a number of ways, depending on the size, number, and configuration of the devices, or according to physician or patient preference. FIGS. 2–4 depict one such delivery system 44 in which first and second intragastric members 24, 25 are mounted over a plastic overtube 18 and secured by a series of suture ties 43, such as cotton thread. A wire guide 19 is typically used in the procedure, and is placed through the passageway 52 of the overtube 18. As shown in FIG. 3, the overtube 18 includes a plurality of apertures 21, a pair of which (e.g., apertures 22 and 23) are distributed approximately every 2 cm along the distal portion of the overtube 18. To secure the intragastric members 24, 25, the suture tie is pulled through the first aperture 22 using a device 42 such as a loop, hook, snare, etc. It is fed through a releasing mechanism 20, such as the illustrative wire loop, and then pulled through the opposite aperture 23. The intragastric members 24, 25 are then placed on the overtube 18, and the suture ties 43 are secured, thereby constraining the intragastric members into a first configuration 14 for delivery. Once the delivery system 44 has been introduced into the gastric lumen, the releasing mechanism 20 is pulled back through the overtube 18, thereby severing the suture ties 43 one by one and releasing the intragastric members 11 into the gastric lumen where they can assume a second configuration 15 (see FIG. 1) that is sufficiently voluminous such that they cannot pass from the stomach.

Figure 5:
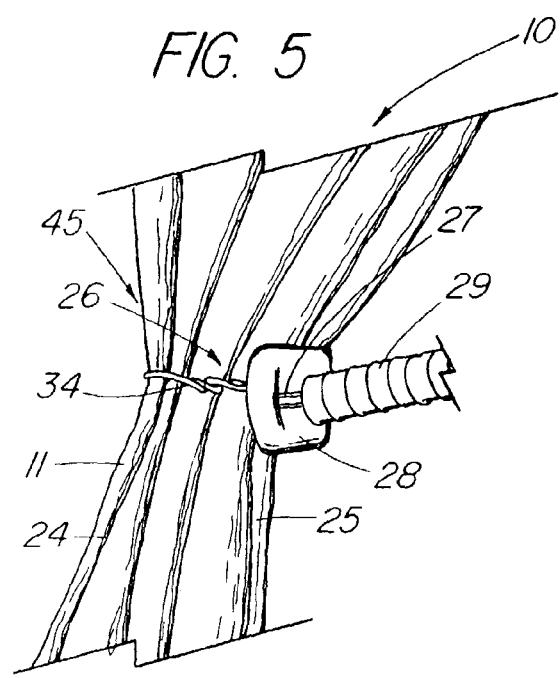

In order to create an obesity treatment apparatus 10 that will be retained in the stomach, it may be necessary that the intragastric members 11 be coupled together to form a grouping or set 45 of intragastric members. FIG. 4 shows the two deployed intragastric members 24, 25 that each have a coupling mechanism 26 (tether 27) attached about them such that they can be drawn together as depicted in FIG. 5. A push member 29, such as a corrugated metal tube, is placed into gastric lumen by using an endoscope, and is guided over the tethers 27 to urge a securing element 28, such as a rubber patch, tightly against the two intragastric members 24, 25. The tethers 27 can then be cut, allowing the grouping 45 to float free within the stomach. This method can also be used to join additional intragastric members 11 to form a larger grouping 45. Likewise, the illustrative delivery system 44 of FIG. 2 can be used to deliver any practical number of intragastric members 11, which can then be joined in the manner described above, or they can be delivered singly or in pairs, and then grouped together after all of the intragastric members 11 have been placed.

Figure 9:
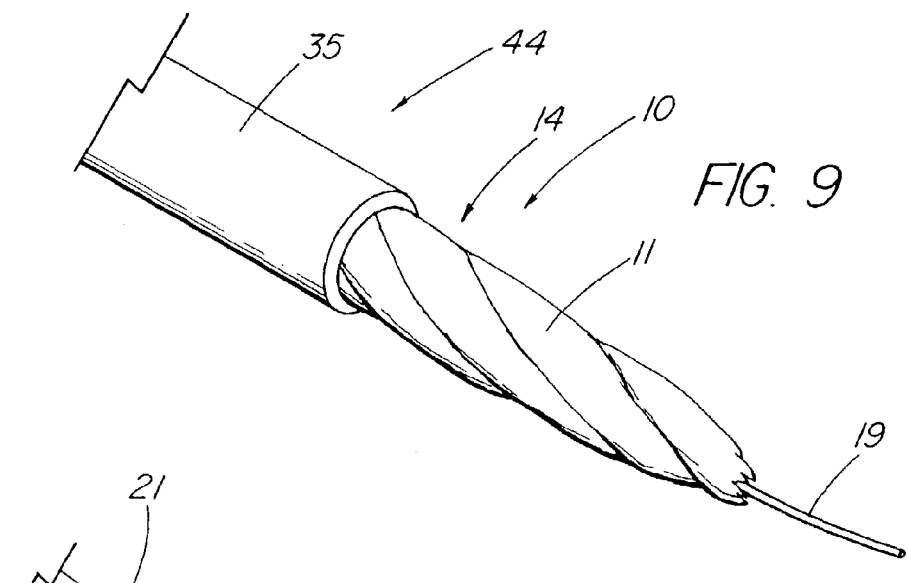
FIG. 9 depicts a pictorial view of an intragastric member of the present invention being delivered from an outer catheter.
Figure 10:
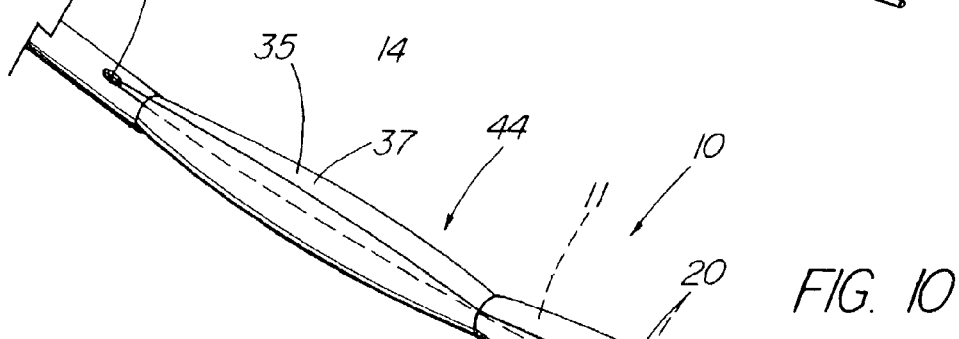
FIG. 10 depicts a pictorial view of an intragastric member of the present invention that includes a splittable outer sheath.
Figure 11:
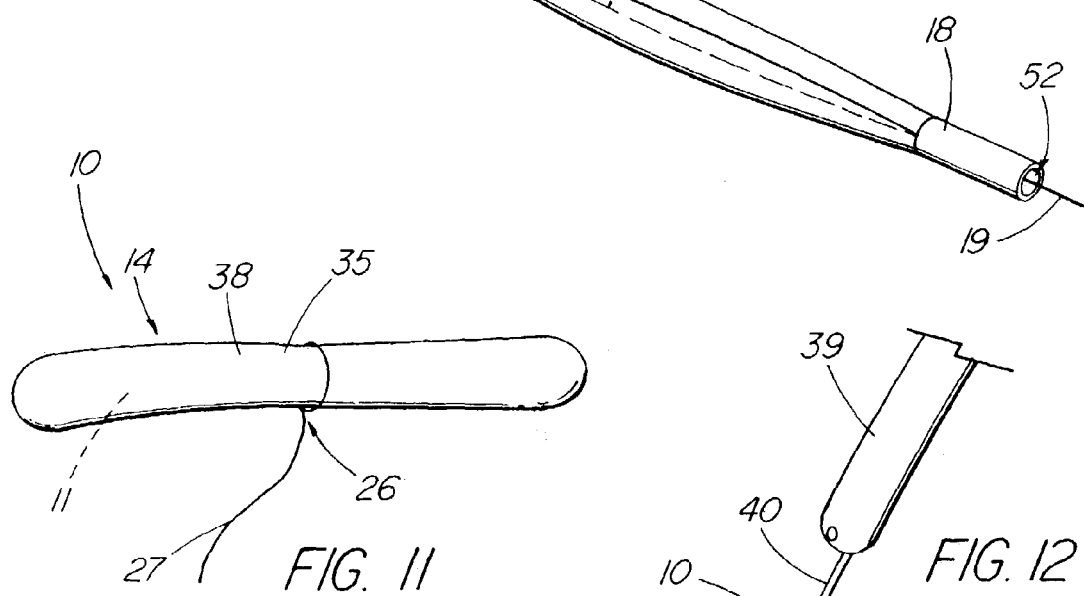
FIG. 11 depicts a side view of an intragastric member of the present invention encased in a dissolvable outer package.

FIGS. 9–11 depict intragastric members 11 that are delivered into the gastric lumen within an outer member 35, such as a sheath, tube, package, wrapping, etc., and subsequently released. For example, FIG. 9 depicts a delivery system 44 in which the intragastric member 11 (or multiple devices) is preloaded into an outer tube or introducer, then deployed therefrom by being pushed out by using a pusher member (not shown). The intragastric member 11 is shown twisted to aid in loading and deployment.

FIG. 10 depicts a delivery system 44 in which the intragastric member is loaded over a tube 18 (as in FIG. 2), but is secured by an outer member 35 comprising a splittable sheath 37 or sleeve made of a thin plastic material. In the illustrative embodiment, the releasing mechanism 20 comprises a nylon thread or wire that is looped under and over the sheath 37, such that it can be withdrawn to tear through the thin material of the sheath 37 to release the intragastric member(s) 11 mounted on the tube 18. The releasing mechanism of FIG. 10 feeds into an aperture 21 and passageway 52 of the tube 18, where it extends to the proximal end of the apparatus 10. Other types of splittable sheaths 37 can also be used, such as the COOK® PEEL-AWAY Introducer Sheath.

FIG. 11 depicts an intragastric member 11 that includes an outer member 35 comprising a dissolvable enclosure 38. The material, such as cellulose, gelatin, or some other dissolvable or rapidly degrading synthetic or biomaterial material, allows the intragastric member 11 to be deployed in the first configuration 14 into the stomach, where it expands into the second configuration 15 (see, e.g., FIG. 1) once the outer enclosure 38 has dissolved or degraded away. The embodiment of FIG. 11 can be delivered with or without a catheter-based delivery system 44, or swallowed by the patient, depending on the outer dimensions of the apparatus 10.

Figure 12:
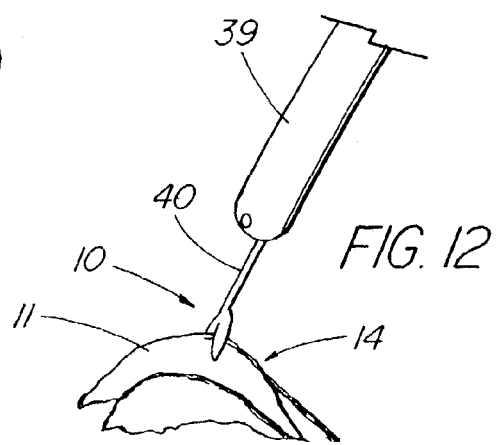
FIG. 12 depicts a pictorial view of an intragastric member of the present invention being manipulated by a endoscopic device.

FIG. 12 also depicts a method of delivering the apparatus 10 of the present invention without a catheter or tube 18. It has been found that the intragastric members 11 can be pulled into the gastric lumen using an endoscope 39 and endoscopic instrument 40, such as a forceps, basket, snare, etc. This technique can be employed to pull groupings 45 (see, e.g., FIG. 4) of intragastric members 11 into the gastric lumen, as long as the alimentary tract is sufficiently wide to accommodate the grouping 45.

Figure 13:
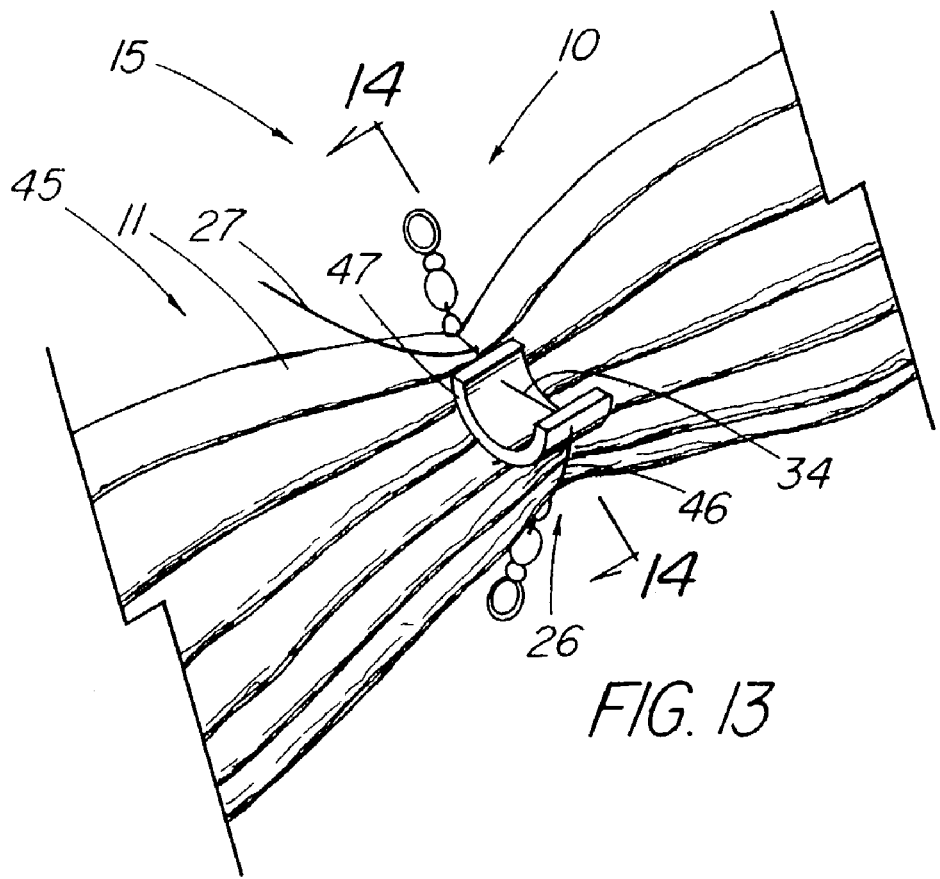
FIG. 13 depicts a set of intragastric members of the present invention bundled together by a coupling mechanism.
Figure 14:
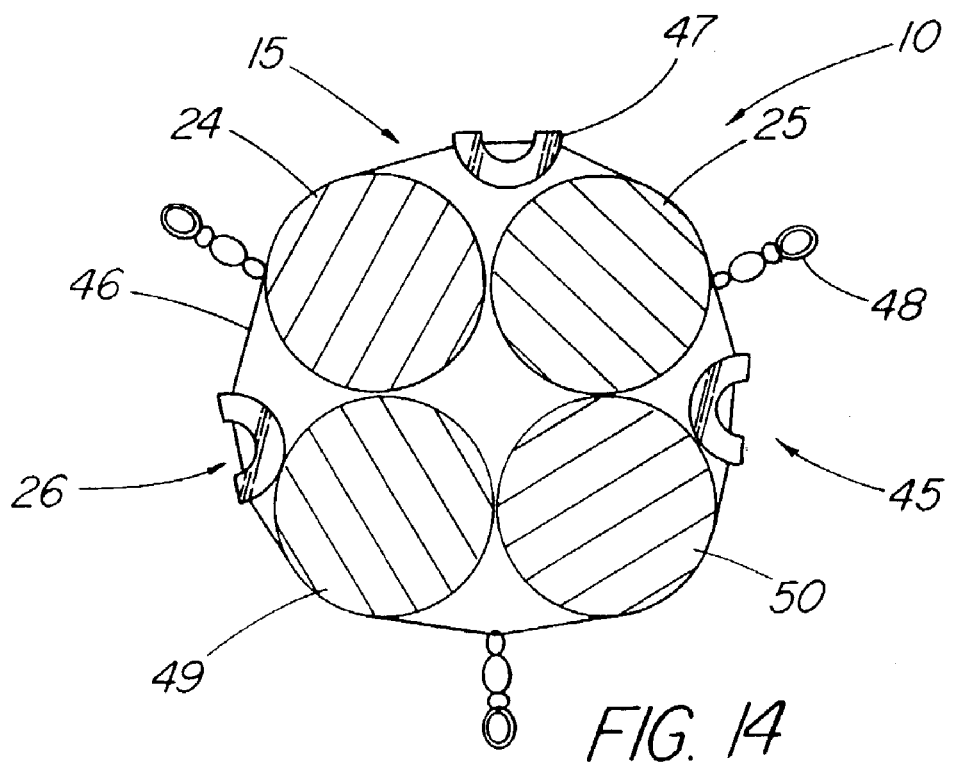
FIG. 14 depicts a schematic cross-sectional view taken along line 13—13 of FIG. 13.

FIGS. 13–14 depict a grouping 45 of four intragastric members 24, 25, 49, 50 that are pre-coupled to one another by a coupling mechanism 26 prior to introduction into the gastric lumen. Although such an arrangement or grouping 45 is sufficiently small such that it can be introduced into the gastric lumen as a set, the adherence of mucous and other changes that occur within the stomach environment can, over time, significantly increase the volume of the apparatus 10 from, for example, an original size of about 60 ml up to a possible size of about 150 ml. The increased size can make it very difficult to remove the grouping 45 from the stomach. To address this problem, multiple intragastric members 45 are grouped together for introduction, and then cut apart when it is time to remove them from the patient. The coupling mechanism 26 comprises a grouping mechanism 46, such as a nylon thread (e.g., standard nylon fishing line), that is wrapped around the grouping 45 to pull them into close contact with one another. The grouping is released by severing the line comprising the grouping mechanism 46 and the intragastric members 24, 25, 49, 50 are removed one at time using a retrieval device such as that shown in FIG. 12.

To assist the operator in cutting the line 46 to release the grouping 45, two different coupling components 47, 48 are included in the illustrative embodiment. The first coupling component 47 comprises a curved polymer piece which is traversed by the line 46 in such a manner that the line 46 can be readily visualized under the scope, thereby providing a place to grasp and/or cut the line with an instrument extending from the endoscope. The second coupling component 48 comprises a fishing line swivel, which being metal, can be readily visualized, as well as providing a hard surface against which a cutting instrument can be applied to sever the line 46, especially if the line has proved difficult to cut using other methods. It also provides an easily accessible point on the apparatus 10 which can be grabbed with a forceps or other device.

Figure 15:
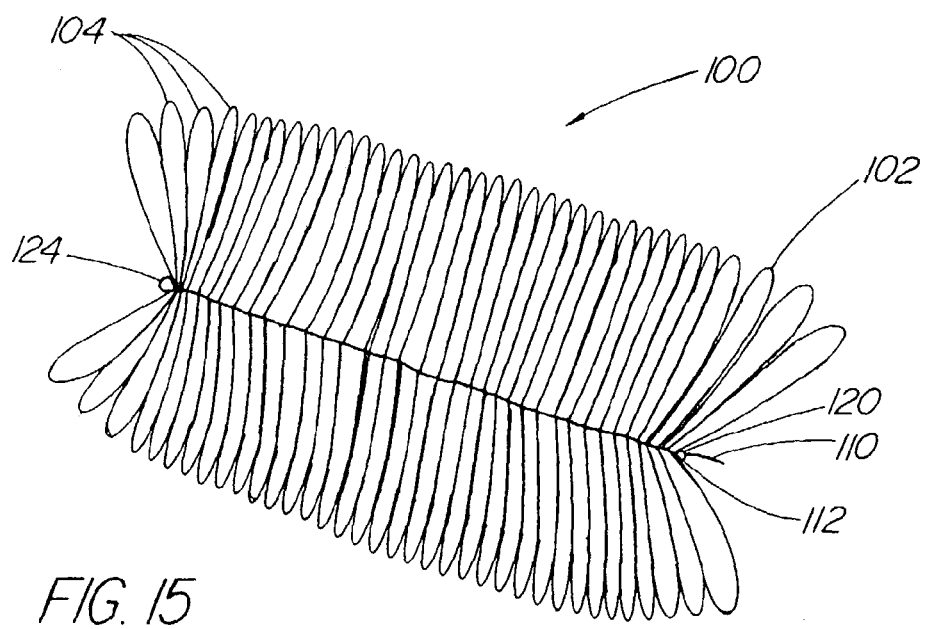
FIG. 15 depicts a pictorial view of another embodiment of an intragastric member of the present invention.
Figure 17:
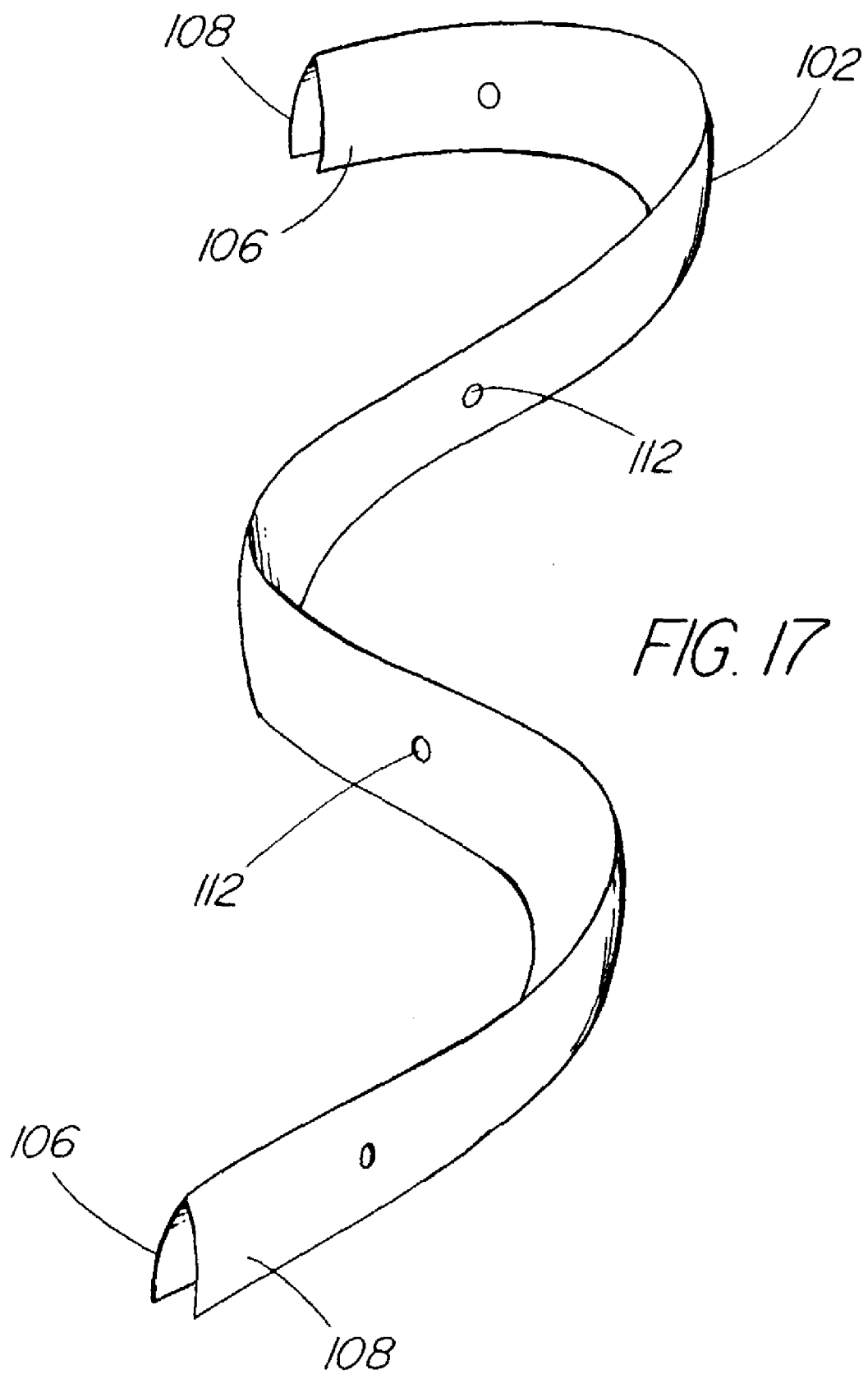
FIG. 17 depicts a portion of the strip material that is used to form the embodiment of FIG. 15.

FIG. 15 depicts another embodiment of an intragastric member 100 of the present invention. In this embodiment, the intragastric member 100 comprises a single strip of high-density polyethylene 102 that has been folded and bundled to form eighty-nine (89) loops 104 in the general shape of a butterfly. As best seen in FIG. 17, the single strip of high-density polyethylene 102 of the embodiment is formed from a tube of material having a wall thickness of 7.5 microns and a perimeter of 6 cm that has been sliced in half. Each half of the material is then folded to form a strip 102 having two walls 106, 108, wherein each wall 106, 108 has a width of 1.5 cm. Of course, the strip 102 could comprise a different number of walls 106, 108, have a different width and thickness, or be formed from a tube of material.

In the embodiment of the intragastric member 100 shown in FIG. 15, each loop 104 is 40 cm in length. Accordingly, the intragastric member 100 is formed from single strip 102 having a total length of approximately 35.6 m.

The intragastric member 100 is bundled by passing a nylon thread 110 through an aperture 112 in the strip 102 at the center of the each loop 104. As best seen in FIG. 17, the apertures 112 are formed in each wall 106,108 of the strip 102, and are spaced so that loops 104 are formed 40 cm in length when adjacent apertures 112 are pulled together to form the intragastric member 100 shown in FIG. 15. In other words, the apertures 112 are located every 40 cm along the length of the strip 102.

Figure 16:
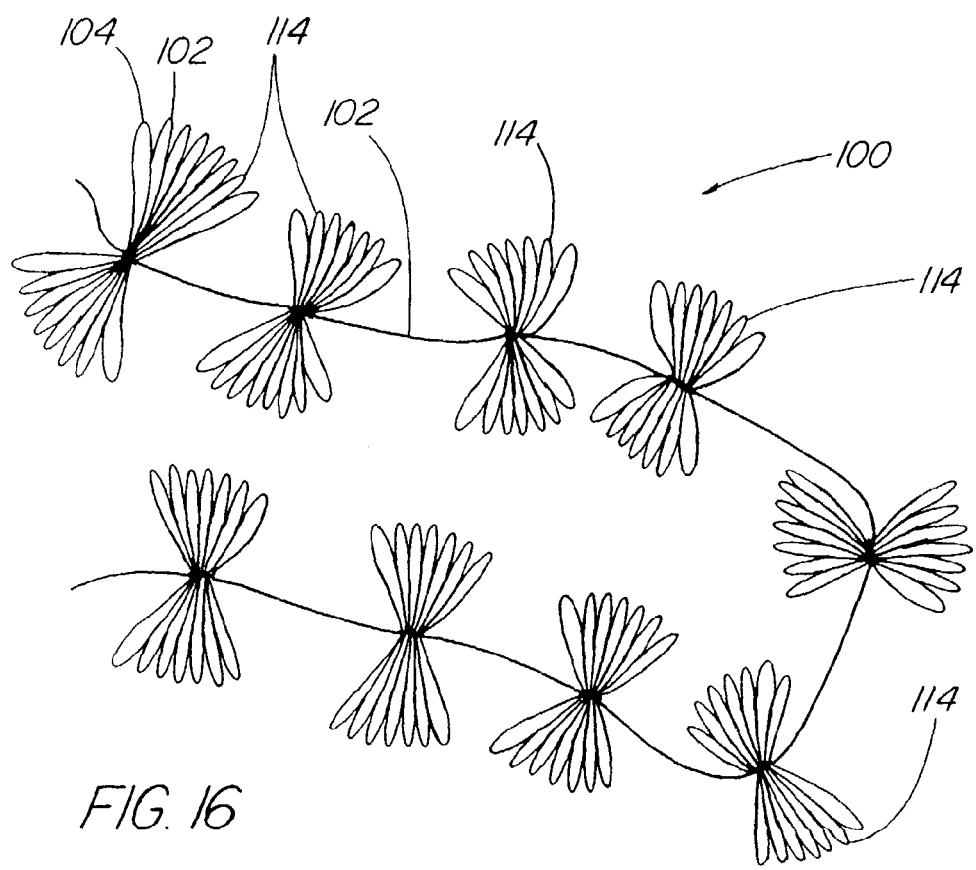
FIG. 16 depicts a pictorial view of the embodiment of FIG. 15 separated into separate bundles and ready for insertion into the gastric lumen.

The embodiment of the intragastric member 100 shown in FIG. 15 may be too large for delivery or insertion into the gastric lumen while in its bundled, final configuration. Accordingly, the intragastric member 100 is preferably inserted into the gastric lumen is stages. For example, and as shown in FIG. 16, the intragastric member 100 is separated into nine (9) separate bundles 114, each of which comprise approximately ten (10) loops 104 of the strip 102. The loops 104 of each separate bundle 114 are temporarily grouped or held together by a twist tie 116 or similar device. Grouping the separate bundles 114 in this manner improves the handling of the material and prevents the strip 102 from becoming tangled or contaminated.

Figure 18:
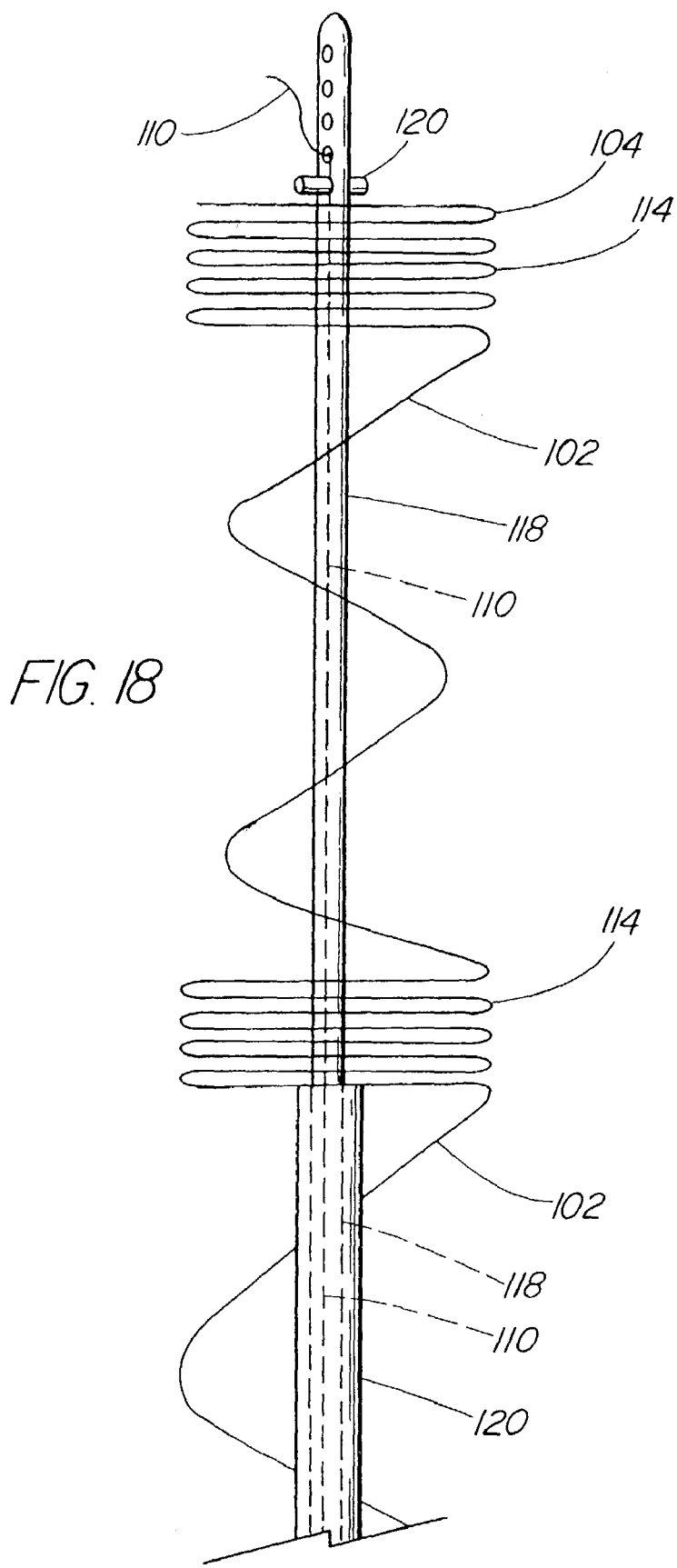
FIG. 18 depicts the insertion of the separate bundles of FIG. 16 being inserted into the gastric lumen

As shown in FIG. 18, the separate bundles 114 of the intragastric member 100 are inserted into the gastric lumen one at a time by using a wire guide 118 such as a Savary-Gilliard™ wire guide, manufactured by Wilson-Cook Medical Inc., Winston-Salem, N.C. The wire guide 118 comprises a central opening through which the nylon thread 110 passes. The end of the nylon thread 110 is connected to or tied around a small piece of nylon tubing 120 that is sized so as to not pass through the apertures 112 in the strip 102. Prior to the insertion procedure, the nylon tubing 120 is placed near the distal (forward or insertion) end of the wire guide 118 so as to prevent the strip 102 of the first bundle 114 from sliding off the end of the wire guide 118.

Once the distal end of the wire guide 118 is positioned in the gastric lumen, the first bundle 114 is threaded over the proximal (rearward) end by passing the apertures 112 over the wire guide 118. A plastic tube 122 is then positioned over the proximal end of the wire guide 118, and slid towards the distal end of the wire guide 118 so as to push the folds 104 of the first bundle against the nylon tubing 120. This procedure is then repeated by threading subsequent bundles 114 over the wire guide 118 and pushing them against the previously inserted bundles 114 until all of the bundles 114 have been inserted into the gastric lumen. The bundles 114 are then secured together by pushing a small rubber stopper or similar device 124 (see FIG. 15) along the wire guide 118 so as to press against the last bundle 114 to be inserted. The wire guide 118 is then withdrawn so as to leave the nylon thread 110 extending through the apertures 112 of all of the bundles 114. The nylon thread 110 is then tied or otherwise secured to the stopper 124 so as to form a complete intragastric member 100 as shown in FIG. 15.

To remove the intragastric member 100 from the gastric lumen, the nylon thread 110 is typically cut so as to release the folds 104. One end of the strip 102 is then grasped by an endoscopic or similar device and pulled out of the patient.

Figure 19:
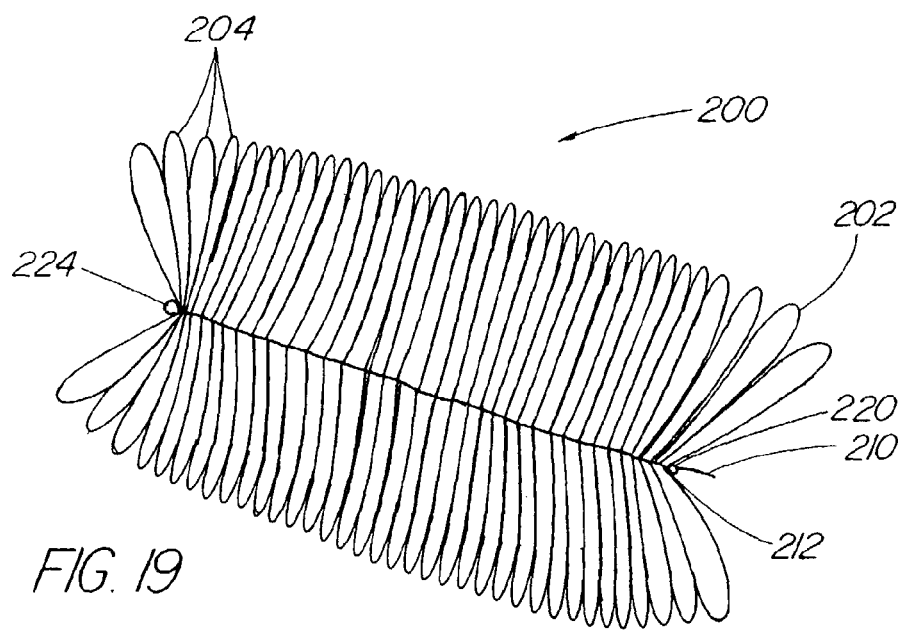
FIG. 19 depicts a pictorial view of yet another embodiment of an intragastric member of the present invention.
Figure 21:
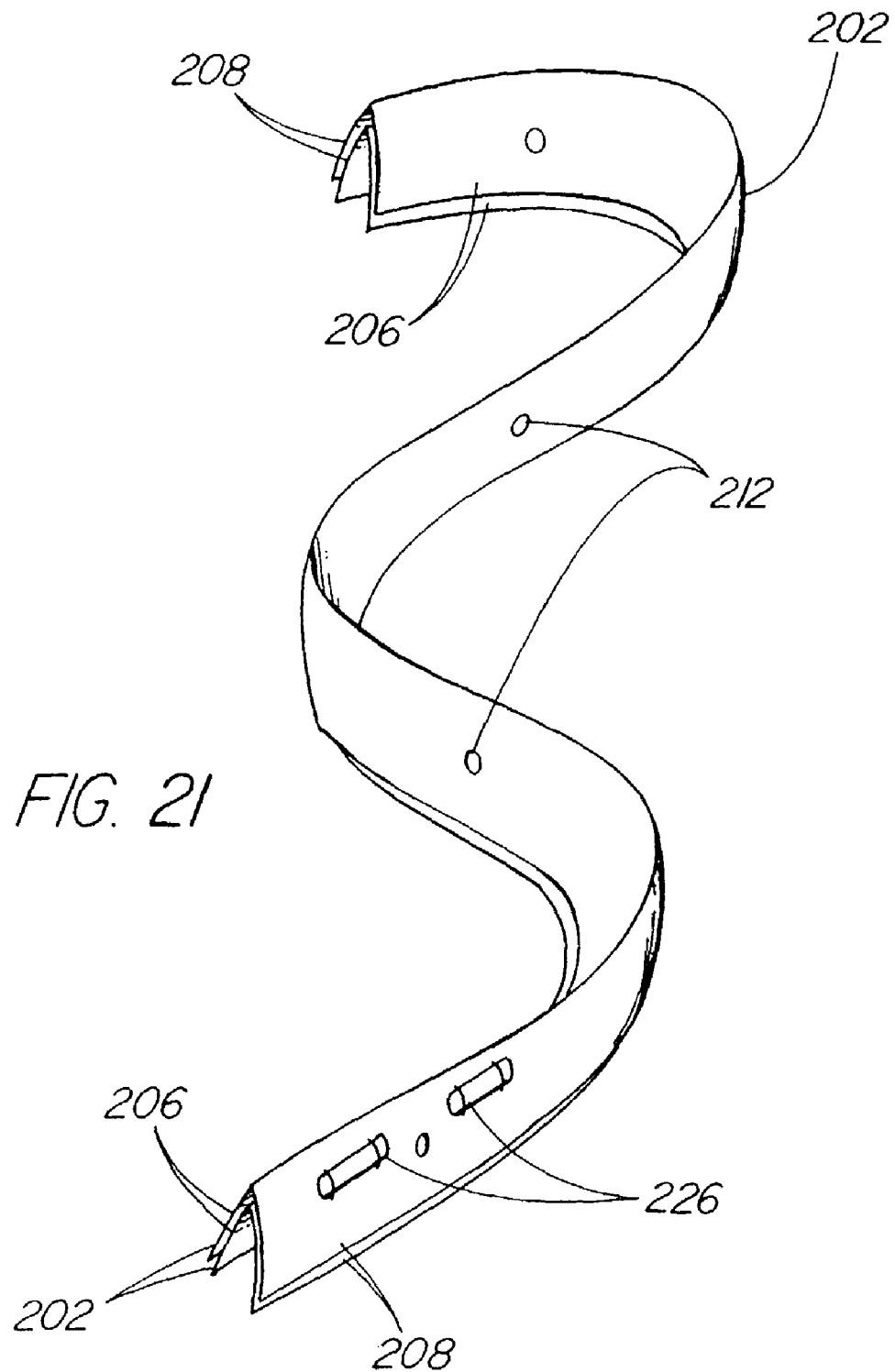
FIG. 21 depicts a portion of the strip material that is used to form the embodiment of FIG. 19.

FIG. 19 depicts yet another embodiment of an intragastric member 200 of the present invention. In this embodiment, the intragastric member 200 comprises a double strip of low-density polyethylene 202 that has been folded and bundled to form approximately forty-five (45) loops 204 in the general shape of a butterfly. As best seen in FIG. 21, the double strip of low-density polyethylene 202 of this embodiment comprises a pair of strips 202 each having two walls 206, 208, wherein each wall 206, 208 has a width of 15 mm and thickness in the range of 40–50 microns.

In the embodiment of the intragastric member 200 shown in FIG. 19, each loop 204 is 20 cm in length. Accordingly, the intragastric member 200 is formed from a double strip 202 of material having a total length of approximately 18 m (i.e., each strip 202 has a total length of approximately 18 m). A double strip 202 having longer or shorter lengths may also be used depending on the desired size and mass of the intragastric member 200.

The intragastric member 200 is bundled by passing a nylon thread 210 through an aperture 212 in each strip 202 at the center of the each loop 204. As best seen in FIG. 21, the apertures 212 are formed in each wall 206, 208 of each strip 202, and are spaced so that loops 204 are formed 20 cm in length when adjacent apertures 212 are pulled together to form the intragastric member 200 shown in FIG. 19. In other words, the apertures 212 are located every 20 cm along the length of the strip 202. In the preferred embodiment shown, apertures 212 have a diameter of approximately 3.5 mm.

Figure 20:
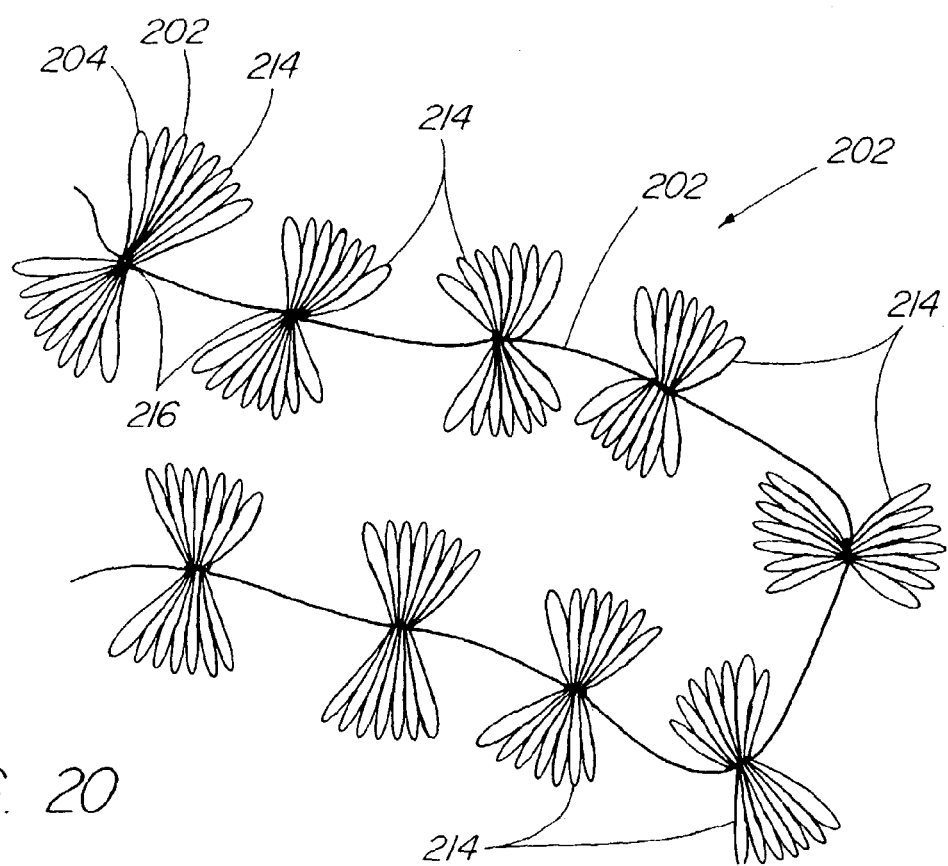
FIG. 20 depicts a pictorial view of the embodiment of FIG. 19 separated into separate bundles and ready for insertion into the gastric lumen.

The embodiment of the intragastric member 200 shown in FIG. 19 may be too large for delivery or insertion into the gastric lumen while in its bundled, final configuration. Accordingly, the intragastric member 200 is preferably inserted into the gastric lumen is stages. For example, and as shown in FIG. 20, the intragastric member 200 is separated into nine (9) separate bundles 214, each of which comprise approximately five (5) loops 204 of the strip 202. The loops 204 of each separate bundle 214 are grouped or held together by a breakable tie 216, made of cotton thread, or similar device. As will be explained below, grouping the separate bundles 214 in this manner improves the handling of the material and prevents the strips 202 from becoming tangled or contaminated during the insertion thereof.

Figure 22:
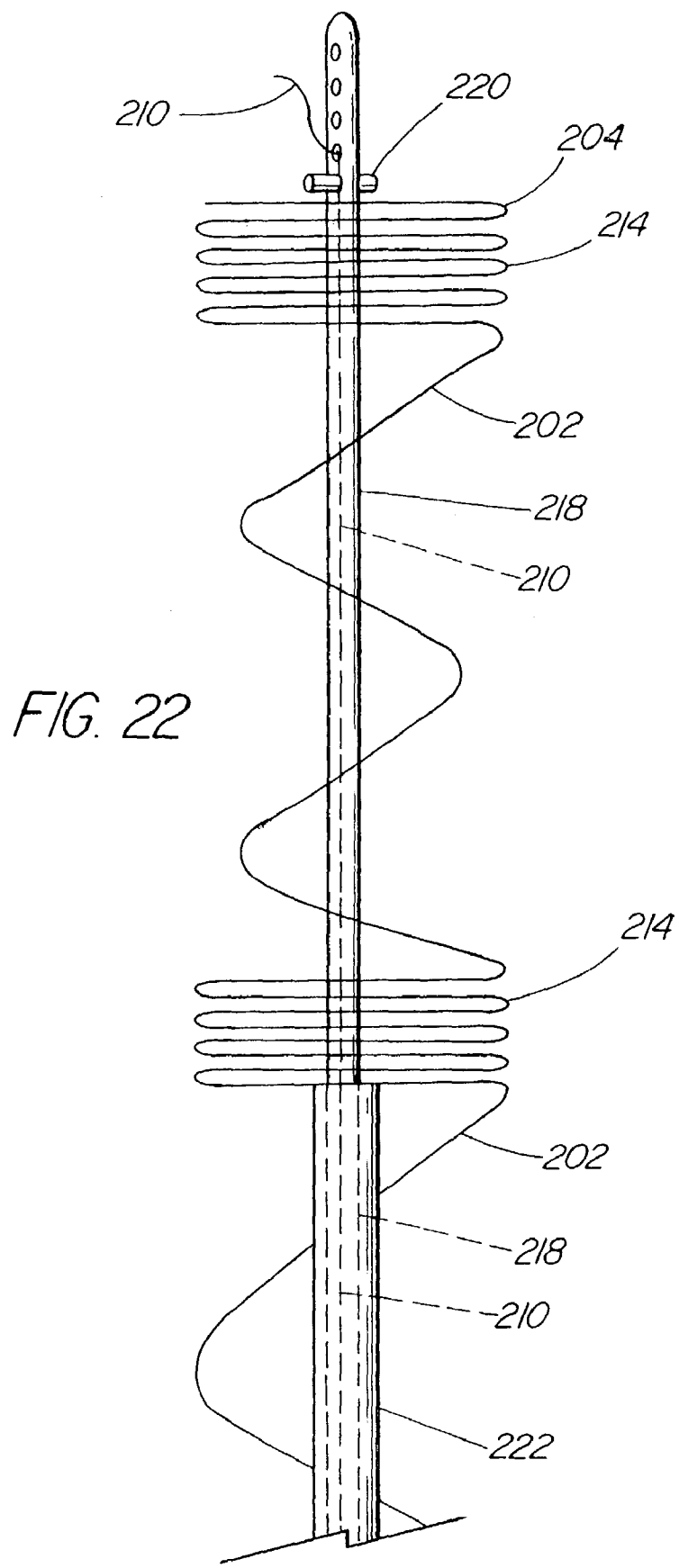
FIG. 22 depicts the insertion of the separate bundles of FIG. 20 being nserted into the gastric lumen.

As shown in FIG. 22, the separate bundles 214 of the intragastric member 200 are inserted into the gastric lumen one at a time by using a wire guide 218 such as a Savary-Gilliard™ wire guide, manufactured by Wilson-Cook Medical Inc., Winston-Salem, N.C. The wire guide 218 comprises a central opening through which the nylon thread 210 passes. The end of the nylon thread 210 is connected to or tied around a small nylon disc 220 that is sized so as to not pass through the apertures 212 in the strips 202. Prior to the insertion procedure, the nylon disc 220 is placed near the distal (forward or insertion) end of the wire guide 218 so as to prevent the strips 202 of the first bundle 214 from sliding off the end of the wire guide 218.

Once the distal end of the wire guide 218 is positioned in the gastric lumen, the first bundle 214 is threaded over the proximal (rearward) end by passing the apertures 212 over the wire guide 218. A pusher tube 222, which may be plastic, metal or some other suitable material, is then positioned over the proximal end of the wire guide 218, and slid towards the distal end of the wire guide 218 so as to push the folds 204 of the first bundle 214, which remain bundled by tie 216, against the nylon disc 220.

In the preferred embodiment shown, one or more of the apertures 212 in each bundle 214 have an increased diameter that is sufficient to allow one more folds 204 to slide over the outside of the pusher tube 222. This permits the portion of the strips 202 connected between adjacent bundles 214 to be guided (extended) along the wire guide 218 without interfering with the deployment of each bundle 214. In the preferred embodiment shown, those apertures 212 having an increased diameter are approximately 9–10 mm in diameter.

This procedure is then repeated by threading subsequent bundles 214 over the wire guide 218 and pushing them against the previously inserted bundles 214 until all of the bundles 214 have been inserted into the gastric lumen. The bundles 214 are then secured together by pushing a small rubber stopper or similar device 224 (see FIG. 19) along the wire guide 218 so as to press against the last bundle 214 to be inserted. The wire guide 218 is then withdrawn so as to leave the nylon thread 210 extending through the apertures 212 of all of the bundles 214. The nylon thread 210 is then tied or otherwise secured to the stopper 224 so as to form a complete intragastric member 200 as shown in FIG. 19.

To remove the intragastric member 200 from the gastric lumen, the nylon thread 210 is typically cut so as to allow the intragastric member 200 to separate in separate bundles (see FIG. 20). The separate bundles 214, which remain connected to each other by strips 202, can then be removed one at a time. In the event that the removal of the intragastric member 200 in separate bundles 214 becomes difficult or problematic, then breakable ties 216 may be severed to release the folds 204 of one or more of the bundles 216.

As best seen in FIG. 21, visual markers 226, such as colored tubing, are sutured to the side of the strips 202 of the first or last fold 204 on either side of the aperture 212. These markers 226 assist the physician in locating the nylon thread 210, which may be difficult to identify after the device has resided within the gastric lumen for an extended period of time. Once the nylon thread 210 is cut, one end of the pair of strips 202, or one of the bundles 216, is then grasped by an endoscopic or similar device and pulled out of the patient.

Figure 23:
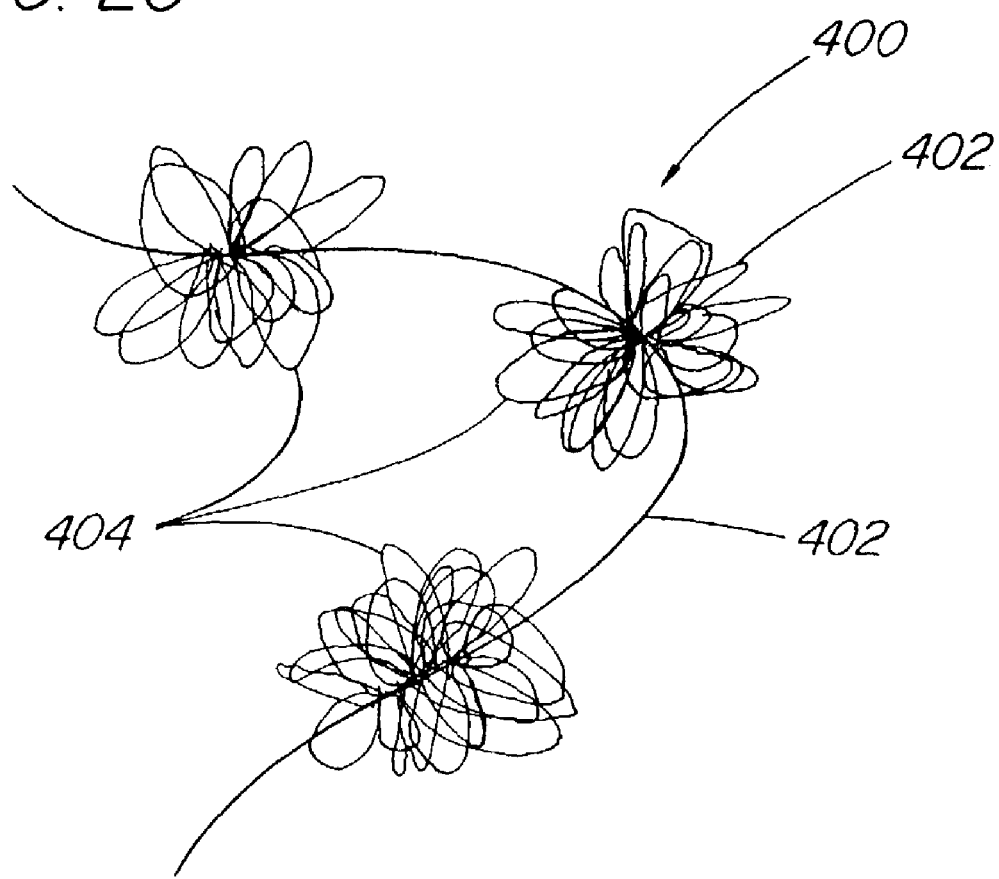
FIG. 23 depicts a pictorial view of yet another embodiment of an intragastric member of the present invention.

FIG. 23 depicts yet another embodiment of an intragastric member 400 of the present invention. In this embodiment, the intragastric member 400 comprises nylon thread 402 that has been tied into a series of nylon balls 404. The nylon balls 404 are inserted into the gastric lumen separately and then connected together to form a single, larger mass of nylon thread (not shown).

Figure 24:
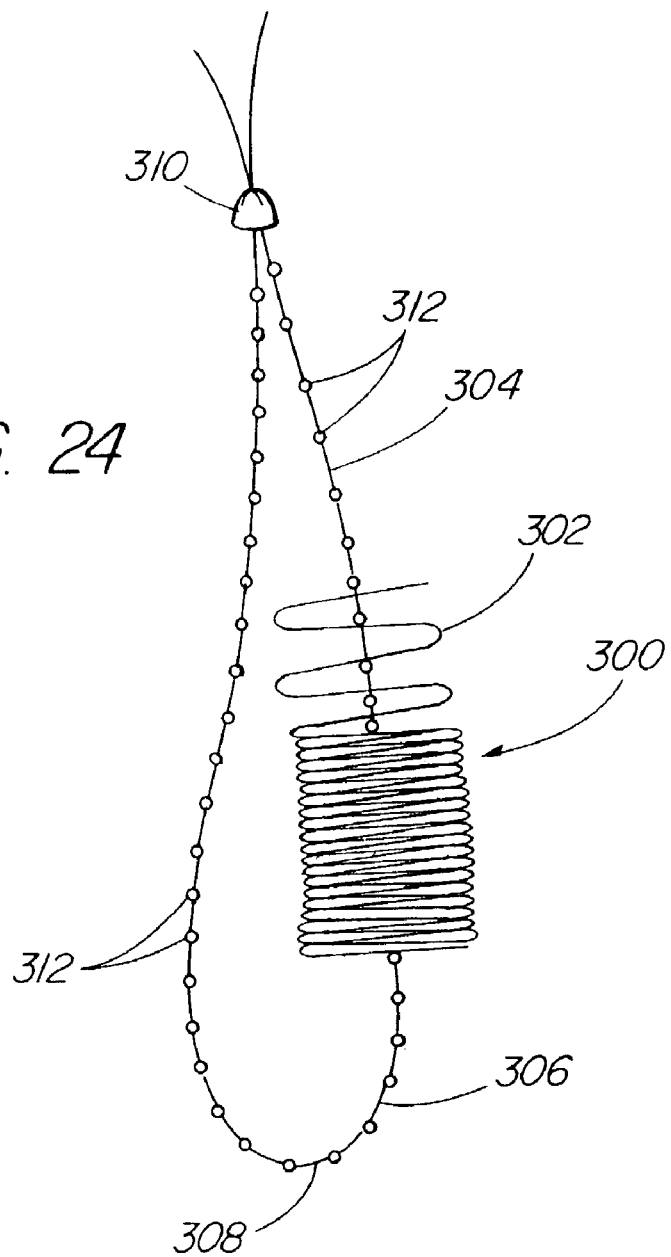
FIGS. 24 and 25 depict an alternative method of inserting of an intragastric member of the present invention into the gastric lumen.
Figure 25:
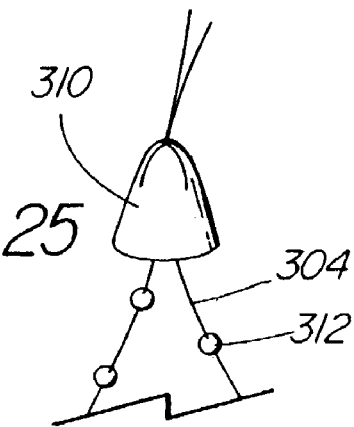

The above-described embodiments, particularly the embodiments of FIGS. 15 and 19, can be deployed using alternative procedures. For example, and as shown in FIGS. 24 and 25, the intragastric member 300 could be deployed by extending the strip 302 along a nylon thread 304 that has been formed into a loop 306. Once the end 308 of the loop 306 has been inserted into the gastric lumen, then a locking device 310, such as plastic cone (shown in detail in FIG. 25), is pushed over both strands of the nylon thread 304 so as to close the loop 306. As the loop 306 is closed, the strip 302 is compressed so as to form an intragastric member 300 having a configuration similar to that shown in FIGS. 15 and 19. Knots 312 are included along the nylon thread 304 to provide a ratcheting action with the locking device 310. After the intragastric member 300 has been deployed inside the gastric lumen, then the portion of the nylon thread 304 extending beyond the locking device 310 can be severed with an endoscopic scissors and removed.

Alternatively, the strip 302 can be compressed by sliding a tube (not shown) along one or both halves of the loop 306. In addition, the intragastric member 300 can be inserted in bundles (see FIGS. 16 and 20), as opposed to the insertion of a single strip 302 of material (as described above).

An anchor stent (not shown) could be utilized to temporarily secure the end of the nylon thread 304 (or the end 308 of the loop 306) inside the gastric lumen during the insertion procedure. For example, an anchor stent enclosing a portion of the nylon thread 304 would be inserted into the pylorus and lodged therein. One end of the nylon thread 304 (or loop 306) enclosed within the anchor stent is then removed therefrom and pulled out of the subject. The other end of the nylon thread 304 (or loop 306) remains attached to the anchor stent. The intragastric device 300 can then be inserted into the gastric lumen by pushing or sliding the strip 302 (or bundles) down the nylon thread 304 (or loop 306), the end of which remains secured within the gastric lumen by the anchor stent. Once the insertion procedure is removed, then the anchor stent and any excess nylon thread 304 is removed.

Experimental testing of the present invention has been conducted on mammals. In particular, an embodiment of an intragastric member similar to the embodiment shown in FIGS. 19–21 was inserted into the gastric lumens of a group of ten (10) pigs for a period of 49 days. No deaths or major complications were observed in any of the test subjects. The initial weight for the test subjects was measured to be in the range of 25.0 to 31.2 kg, with an average weight of 27.8 kg. At the end of the 49 day testing period, the weight of the test subjects was measured to be in the range of 29.5 to 39.0 kg, with an average weight of 34.5 kg. The anticipated weight for the test subjects at the end of the testing period, in view of the normal and expected growth for these animals, was 57 kg. Accordingly, the test subjects gained an average weight that was significantly less than the weight gain observed in similar animals without the intragastric member.

Any other undisclosed or incidental details of the construction or composition of the various elements of the disclosed embodiment of the present invention are not believed to be critical to the achievement of the advantages of the present invention, so long as the elements possess the attributes needed for them to perform as disclosed. The selection of these and other details of construction are believed to be well within the ability of one of even rudimentary skills in this area, in view of the present disclosure. Illustrative embodiments of the present invention have been described in considerable detail for the purpose of disclosing a practical, operative structure whereby the invention may be practiced advantageously. The designs described herein are intended to be exemplary only. The novel characteristics of the invention may be incorporated in other structural forms without departing from the spirit and scope of the invention.

The invention claimed is:

1. A non-balloon intragastric device for the treatment of obesity, the intragastric device comprising a digestive-resistant material that is expandable from a first configuration to a second configuration, the first configuration being sufficiently small to permit introduction of said intragastric device into a gastric lumen of a mammal, the second configuration being sufficiently large to prevent said intragastric device from passing through the mammal's pylorus, wherein said intragastric device is configured to function as an artificial bezoar, and further wherein said digestive-resistant material comprises a continuous strip of material that has been folded to form a plurality of loops, said plurality of loops being connected together to form a shape suggestive of a butterfly or bow-tie.

2. The intragastric device according to claim 1 wherein said digestive-resistive material comprises one or more elements selected from the group consisting of plastic, nylon, polyesters, polyurethanes, polyethylenes, polyamides, silicone and biocompatible polymers to which food will generally not adhere.

3. The intragastric device according to claim 1 wherein said digestive-resistive material comprises one or more elements selected from the group consisting of high-density polyethylene, low-density polyethylene, fluorinated ethylene propylene and ethylene vinyl acetate copolymer.

4. The intragastric device according to claim 1 wherein the digestive-resistant material has a resilience which is biased towards the second configuration.

5. The intragastric device according to claim 1 wherein the continuous strip of material is folded to form a plurality of bundles in the first configuration, each of said bundles comprising a plurality of loops connected together to form a shape suggestive of a butterfly or bow-tie, and wherein said plurality of bundles are connected together in the second configuration.

6. The intragastric device according to claim 5 wherein each of the bundles is introduced into the gastric lumen of the mammal separately.

7. The intragastric device according to claim 1 wherein the plurality of loops are connected together with a nylon thread that passes through an aperture in each loop.

8. The intragastric device according to claim 1 wherein the continuous strip of material comprises a flattened tube of material.

9. The intragastric device according to claim 1 wherein the continuous strip of material comprises a folded strip of material.

10. The intragastric device according to claim 1 wherein the continuous strip of material comprises a pair of folded strips of material, one strip being nested inside the other.

11. The intragastric device according to claim 1 wherein the intragastric device has been introduced into the gastric lumen of the mammal with an endoscopic device.

12. The intragastric device according to claim 1 wherein the intragastric device has been introduced into the gastric lumen of the mammal in stages, wherein a sub-component of the intragastric device is introduced into the gastric lumen in each stage, said sub-components being combined with each other in the gastric lumen to form a single intragastric device.

13. The intragastric device according to claim 1 wherein the intragastric device is contained within a delivery catheter when in the first configuration, and is pushed out of the delivery catheter and allowed to expand to form the second configuration.

14. The intragastric device according to claim 1 wherein the intragastric device is contained within a delivery sheath when in the first configuration, and is removed from the delivery sheath and allowed to expand to form the second configuration.

15. The intragastric device according to claim 14 wherein the delivery sheath comprises an outer wrapping that may be split by an operator to permit the intragastric device to expand to form the second configuration.

16. The intragastric device according to claim 14 wherein the delivery sheath comprises an dissolvable material that will dissolve in the gastric lumen to permit the intragastric device to expand to form the second configuration.

17. The intragastric device according to claim 1 wherein said digestive-resistant material is substantially non-elastic.

18. The intragastric device according to claim 1 wherein said digestive-resistant material is substantially non-expandable.

19. The intragastric device according to claim 1 wherein said digestive-resistant material is substantially non-inflatable.

* * * * *